United States Patent [19]

Komoschinski et al.

[11] Patent Number: 5,922,874
[45] Date of Patent: Jul. 13, 1999

[54] PROCESS FOR PREPARING N-ARYL-N'-ALKYL-PIPERAZINES

[75] Inventors: Joachim Komoschinski, Köln; Helmut Fiege, Leverkusen; Bernhard Beitzke, Rösrath, all of Germany

[73] Assignee: Bayer Atkiengesellschaft, Germany

[21] Appl. No.: 09/122,160

[22] Filed: Jul. 24, 1998

[30] Foreign Application Priority Data

Aug. 8, 1997 [DE] Germany ............... 197 34 516

[51] Int. Cl.⁶ ............... C07D 295/13; C07D 295/096; C07D 295/088; C07D 295/073
[52] U.S. Cl. ............................................. 544/395
[58] Field of Search ............................................. 544/395

[56] References Cited

U.S. PATENT DOCUMENTS

| | | | |
|---|---|---|---|
| 2,830,056 | 4/1958 | Ruschig et al. | 544/395 |
| 3,106,557 | 10/1963 | Poppelsdorf et al. | 544/395 |
| 3,326,916 | 6/1967 | Creighton et al. | 260/268 |
| 3,381,009 | 4/1968 | Palazzo et al. | 260/268 |
| 3,637,705 | 1/1972 | Horrom et al. | 544/395 |

FOREIGN PATENT DOCUMENTS

| | | |
|---|---|---|
| 889223 | 2/1962 | United Kingdom . |
| 948767 | 2/1964 | United Kingdom . |

OTHER PUBLICATIONS

Batson, F.M. and C.A. Kraus. "A New Synthesis of N–Monophenylpiperazine." *Journal of the American Chemical Society*, 56(10), 2199–2200 (1934), Oct. 1934.

C. Kremer, "A New Synthesis of N–Phenylpiperazino–N–Beta–Ethanol", *J. Am. Chem. Soc.*, vol. 58, 379 (1936).

Prelog, V and V. Stepán. "Nouvelle Synthèse des Pipérazines N–monalcoylées" *Collection of Czechoslovak Chemical Communications* (1935), pp. 93–96 [in French].

*Primary Examiner*—Michael G. Ambrose
*Attorney, Agent, or Firm*—Brinks Hofer Gilson & Lione

[57] ABSTRACT

N-aryl-N'-alkyl-piperazines are obtained in a particularly simple manner, in good yields and in short reaction times when an aniline is reacted under pressure with an N-alkyl-bishydroxyethyl-amine in the presence of a strong acid.

24 Claims, No Drawings

PROCESS FOR PREPARING N-ARYL-N'-ALKYL-PIPERAZINES

BACKGROUND OF THE INVENTION

The present invention relates to a particularly advantageous process for preparing N-aryl-N'-alkyl-piperazines from anilines and diethanolamines.

N-aryl-N'-alkyl-piperazines are important intermediates for preparing pharmaceutically active compounds for diverse indications. Triazole-[4,3-a]-pyridine derivatives having sedative, hypotensive and analgesic action can be obtained, for example, from N-aryl-N'-halogenopropyl-piperazines by reaction with s-triazolo-[4,3-a]-pyridin-3-one (see U.S. Pat. No. 3,381,009).

A plurality of processes for preparing N-aryl-N'-alkyl-piperazines have been disclosed; however, all of these are unsatisfactory.

According to GB patent specification 889 223 an aniline derivative is initially reacted with ethylene oxide to give the corresponding N-bishydroxyethyl-aniline whose OH groups are subsequently replaced by chlorine, and the resulting N-bischloroethyl-aniline is finally reacted with ethanolamine with formation of a piperazine ring. This process comprises a number of steps and is therefore complicated.

GB patent specification 948 767 and U.S. Pat. No. 3,326,916 describe the reaction of m-trifluoromethylaniline with diethanolamine/hydrogen bromide or bis-2-chloroethylamine to give N-aryl-N'-unsubstituted piperazines. An N'-alkyl substituent has to be introduced separately. This process also comprises several steps and is therefore complicated. In addition, bis-2-chloroethylamine and diethanolamine/hydrogen bromide can only be handled if certain industrial hygiene requirements are met.

Finally, it is known to prepare N-aryl-N'-hydroxyethyl-piperazine by condensation of triethanolamine with aniline in the presence of sulfuric acid, the reaction being carried out by boiling at reflux, i.e. at atmospheric pressure (see J.A.C.S. 58, 379(1936)). The yields that can be obtained are not mentioned. A repetition of the experiment using n-trifluoromethylaniline instead of aniline showed that the yields which can be obtained are low and the reaction times required are long (see Comparative Example).

There is therefore still a demand for a simple process for preparing N-aryl-N'-alkyl-piperazines in good yields and short reaction times.

SUMMARY OF THE INVENTION

This invention, accordingly, provides a process for preparing N-aryl-N'-alkyl-piperazines which comprises reacting an aniline under pressure with an N-alkyl-bishydroxyethyl-amine in the presence of a strong acid.

DESCRIPTION OF THE INVENTION

Suitable anilines are, for example, those of the formula (I)

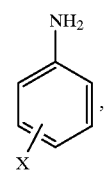

(I)

in which
X represents hydrogen, halogen, $C_1$–$C_4$-alkyl, $C_1$–$C_4$-halogenoalkyl, $C_1$–$C_4$-alkoxy, $C_1$–$C_4$-halogenoalkoxy or nitro.

Halogen, also in the case of halogenoalkyl and halogenoalkoxy, can, for example, mean fluorine, chlorine or bromine.

Preferably X represents fluorine, chlorine, bromine, methyl, ethyl, trifluoromethyl, methoxy, ethoxy, trifluoromethoxy or nitro. Particularly preferably, X represents trifluoromethyl or methoxy.

The substituent X can be in the o-, m- or p-position with respect to the amino group. Preferably, it is in the m-position with respect to the amino group.

The anilines can also be employed in the form of salts, for example as hydrochlorides or hydrosulfates.

Suitable N-alkyl-bishydroxyethyl-amines are, for example, those of the formula (II)

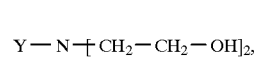

(II)

in which
Y represents optionally substituted $C_1$–$C_4$-alkyl.

Suitable substituents for these alkyl groups are, for example, hydroxyl and amino groups, preferably in a terminal position.

Y preferably represents methyl, ethyl, isopropyl, 2-hydroxyethyl, 3-hydroxypropyl, 2-aminoethyl or 3-aminopropyl.

Particularly preferably, Y represents 2-hydroxyethyl or 3-aminopropyl.

The N-alkyl-bishydroxyethyl-amines can likewise optionally be employed in the form of salts, for example hydrochlorides or hydrosulfates.

When using anilines of the formula (I) and N-alkyl-bishydroxyethyl-amines of the formula (II), N-aryl-N'-alkyl-piperazines of the formula (III)

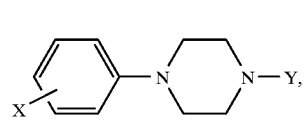

(III)

in which
X and Y have the meanings given for formulae (I) and (II) are obtained.

Suitable strong acids are, for example, 85 to 100% strength by weight sulfuric acid and oleum having an $SO_3$ content of up to 30% by weight (based on $H_2SO_4$). Particular preference is given to 100% strength sulfuric acid, the so-called monohydrate (of $SO_3$).

The process according to the invention can be carried out, for example, at pressures in the range of from 1.5 to 15 bar. Preference is given to 2 to 12 bar.

Appropriate pressures can be set in a variety of ways. For example, the reaction temperature can be selected so that the desired pressure results automatically in a closed vessel. It is also possible to introduce an inert gas, for example nitrogen, carbon dioxide, helium or argon, in such an amount that the desired pressure is reached at the reaction temperature in question. Furthermore, it is possible to add an inert vaporizable solvent and to then select the reaction temperature in such a way that the desired pressure results in the reactor. Solvents which are suitable for this purpose are, for example, straight-chain, branched and cyclic saturated hydrocarbons having, for example, 5 to 15 carbon atoms, such as pentanes, hexanes, heptanes, octanes, decanes, cyclopentane, cyclohexane and decalin.

Suitable reaction temperatures are, for example, those in the range from 130 to 200° C., in particular from 140 to 190° C.

The aniline of the formula (I) and the N-alkyl-bishydroxyethyl-amine can be employed, for example, in molar ratios of 1:0.8 to 1:3. This ratio is preferably at 1:0.9 to 1:1.

0.8 to 2 mol of strong acid can be employed, for example, per mole of aniline of the formula (I) employed. This ratio is preferably at 1:0.9 to 1:1.3.

If an inert vaporizable solvent is employed for generating pressure, for example 5 to 25% by volume, based on the total reaction mixture, can be employed. This amount is preferably 10 to 20% by volume.

The reaction time, i.e. the time for which the reaction mixture is kept under the reaction conditions after the reaction partners and the strong acid have been added can be, for example, 4 to 20 hours, preferably 5 to 12 hours.

The mixture which is present after the reaction has ended can be worked-up, for example, by initially cooling and venting the mixture, followed by neutralization with a base, for example up to a pH in the range of 7 to 11, addition of an organic, water-immiscible solvent, for example an aromatic compound, and removal and distillative work-up of the resulting organic phase.

Using the present invention, N-aryl-N'-alkyl-piperazines can be obtained in a one-step process in short reaction times and good yields. This is surprising, since the use of pressure requires higher reaction temperatures. At higher reaction temperatures, however, a reduction in selectivity and the formation of decomposition products have to be expected.

EXAMPLES

Example 1

100 g of 3-trifluoromethylaniline and 112.3 g of triethanolamine were filled into an autoclave made of tantalum, and 85.2 g of sulfuric acid, 100% strength, were subsequently added by means of a pump. The autoclave was then closed and a nitrogen pressure of 5 bar was applied. The autoclave was then heated to 170° C., resulting in a pressure of 9.2 bar. After a reaction time of 8 h, maximum conversion to N-2-hydroxyethyl-N'-(3-trifluoromethylphenyl)-piperazine was reached. The reaction mixture was cooled and the autoclave was vented, and the mixture was then diluted with water and adjusted to pH 9 using conc. aqueous sodium hydroxide solution. The mixture was then extracted twice with toluene. The organic phases obtained in this manner were worked up by distillation (10 cm Vigreux column), the toluene being removed first. The following second fraction consisted of 63.4 g of unreacted 3-trifluoromethylaniline (bp 48° C. at 2 mbar) which can be used for further reactions, and the last fraction consisted of 51 g of N-2-hydroxyethyl-N'-(3-trifluoromethylphenyl)-piperazine having a boiling range of 150° to 195° C. at 2 mbar.

Example 2 (Comparative Example)

Procedure Corresponding to J.A.C.S. 58, 379 (1936)

100 g of 3-trifluoromethylaniline and 112.3 g of triethanolamine were initially charged in a stirred flask fitted with a reflux condenser. 85.2 g of sulfuric acid, 100% strength, were added dropwise to this mixture and the mixture was heated to reflux (temperature approximately 140° C.). When the reaction was carried out in this manner, maximum conversion to N-2-hydroxyethyl-N'-(3-trifluromethylphenyl)-piperazine was reached after 30 h of reaction time. After a reaction time of 30 h, the mixture was worked up as described in Example 1. During distillation, 65.1 g of m-trifluoromethylaniline were recovered, and 49.5 g of N-2-hydroxyethyl-N'-(3-trifluoromethylphenyl)-piperazine were obtained.

Example 3

100 g of 4-trifluoromethylaniline and 112.3 g of triethanolamine were filled into an autoclave made of tantalum, and 85.2 g of sulfuric acid, 100% strength, were subsequently added by means of a pump. The autoclave was then closed and a nitrogen pressure of 5 bar was applied. The autoclave was then heated to 170° C., resulting in a pressure of 9.5 bar. After a reaction time of 8 h, maximum conversion to N-2-hydroxyethyl-N'-(4-trifluoromethylphenyl)-piperazine was reached. Work-up was carried out as described in Example 1. Unreacted 4-trifluoromethylaniline (62.9 g; bp. 51 ° C. at 2 mbar) was obtained as second fraction, and 49.5 g of N-2-hydroxyethyl-N'-(4-trifluoromethylphenyl)piperazine having a boiling range of 154° to 198° C. at 2 mbar were obtained as last fraction.

Example 4

130.2 g of 3-chloroaniline and 180.8 g of triethanolamine were filled into a tantalum autoclave, and 138.6 g of sulfuric acid, 100% strength, were subsequently added by means of a pump. The autoclave was then closed and heated to 160° C., resulting in an autogenous pressure of 3.3 bar. After a reaction time of 16 h, the contents of the autoclave were worked up as described in Example 1. In this case, 20.64 g of unreacted 3-chloroaniline (bp. 74° to 78° C. at 1.4 to 1.8 mbar) which could be recycled were distilled off initially after the toluene fraction. Subsequently, 105.14 g of N-2-hydroxyethyl-N'-(3-chlorophenyl)-piperazine (boiling range 135° to 188° C., at 1.3 mbar) which solidified at room temperature were obtained.

Example 5

128 g of 3-chloroaniline and 120 g of N-methyl-2,2'-iminodiethanol were initially charged in a tantalum autoclave, and 119 g of sulfuric acid, 100% strength, were added by means of a pump. A nitrogen pressure of 2 bar was subsequently applied and the autoclave was kept at 160° C. (final pressure 4.9 bar) for 15 h. Work-up was carried out as described in Example 1. Distillation gave 69.27 g of unreacted 3-chloroaniline (bp. 64° to 74° C. at 1.1 to 1.7 mbar), and then 60.07 g of N-methyl-N'-(3-chlorophenyl)-piperazine (bp.115° to 130° C. at 1.7 mbar).

Example 6

In this example, the reaction was again carried out as described in Example 1. Here, 123 g of 2-methoxyaniline, 150 g of triethanolamine and 119 g of sulfuric acid, 100% strength, and no nitrogen was blown in. After a reaction time of 15 h at a reaction temperature of 150° C. (autogenous pressure approximately 2.8 bar), work-up was carried out as described in Example 1. Distillation gave 16.6 g of unreacted 2-methoxyaniline (bp. 58° to 91° C. at 1 mbar) and then 99.89 g of N-2-hydroxyethyl-N'-(2-methoxyphenyl)-piperazine (bp. 95° to 173° C. at 1 mbar).

Example 7

Here, 123 g of 2-methoxyaniline, 120 g of N-methyl-2, 2'-iminodiethanol and 119 g of sulfuric acid, 100% strength, were employed. After a nitrogen pressure of 2 bar had been applied (final pressure 4.8 bar), the autoclave was kept at 160° C. for 15 h. Again, work-up was carried out as described in Example 1. 52.71 g of unreacted 2-methoxyaniline (bp. 740 to 80° C. at 1.3 to 1.7 mbar; Vigreux column 10 cm) and 52.1 g of N-methyl-N'-(2-methoxyphenyl)-piperazine (bp. 113° to 127° C. at 2.0 to 2.2 mbar) were obtained.

We claim:

1. A process for preparing N-aryl-N'-alkyl-piperazines, which comprises reacting an aniline under pressure with an N-alkyl-bishydroxyethyl-amine in the presence of a strong acid which is 85 to 100% strength by weight sulfuric acid or oleum having a $SO_3$ content of up to 30% by weight, based on $H_2SO_4$.

2. The process as claimed in claim 1, wherein an aniline of the formula (I) is employed

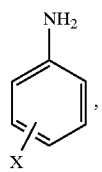

(I)

in which
  X represents hydrogen, halogen, $C_1$–$C_4$-alkyl, $C_1$–$C_4$-halogenoalkyl, $C_1$–$C_4$-alkoxy, $C_1$–$C_4$-halogenoalkoxy or nitro,
an N-alkyl-bishydroxyethyl-amine of the formula (II) is employed

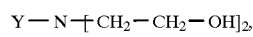

(II)

in which
  Y represents optionally substituted $C_1$–$C_4$-akyl
and an N-aryl-N'-alkyl-piperazine of the formula (III) is obtained

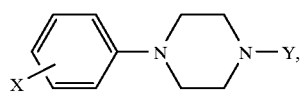

(III)

in which
  X and Y each have the meanings given for formulae (I) and (II).

3. The process as claimed in claim 1, wherein the operating pressure is in the range from 1.5 to 15 bar.

4. The method as claimed in claim 3, wherein the operating pressure is in the range from 2 to 12 bar.

5. The process as claimed in claim 1, wherein the reaction temperature is in the range from 130 to 200° C.

6. The method as claimed in claim 4, herein the reaction temperature is in the range from 140° C. to 190° C.

7. The process as claimed in claim 1, wherein the aniline and the N-alkyl-bishydroxyethyl-amine are employed in molar ratios of 1:0.8 to 1:3.

8. The method as claimed in claim 5, wherein the aniline and the N-alkyl-bishydroxyethyl-amine are employed in molar ratios of 1:0.9 to 1:1.

9. The process as claimed in claim 1, wherein 0.8 to 2 mol of strong acid are employed per mole of aniline employed.

10. The method as claimed in claim 6, wherein 1:0.9 to 1:1 mol of strong acid are employed per mole of aniline employed.

11. The process as claimed in claim 1, wherein the reaction time is from 4 to 20 hours.

12. The method as claimed in claim 7, wherein the reaction time is from 5 to 12 hours.

13. The process as claimed in claim 1, wherein the mixture present after the reaction has ended is worked up by initially cooling and venting the mixture, followed by neutralization with a base, addition of an organic, water-immiscible solvent and removal and distillative work-up of the resulting organic phase.

14. The method as claimed in claim 1, wherein the strong acid used is the monohydrate of $SO_3$.

15. The method as claimed in claim 1, wherein pressure is generated by employing 5 to 25% of an inert vaporizable solvent, based on the total reaction mixture.

16. The method as claimed in claim 15, wherein pressure is generated by employing 10 to 20% of an inert vaporizable solvent, based on the total reaction mixture.

17. The method as claimed in claim 1, wherein said aniline is of the formula (I)

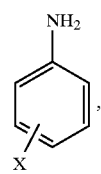

(I)

in which X represents hydrogen, halogen, $C_1$–$C_4$-alkyl, $C_1$–$C_4$-halogenoalkyl, $C_1$–$C_4$-alkoxy, $C_1$–$C_4$-halogenoalkoxy or nitro.

18. The method as claimed in claim 17, wherein X is fluorine, chlorine, bromine, methyl, ethyl, trifluoromethyl, methoxy, ethoxy, trifluoromethoxy, or nitro.

19. The method as claimed in claim 18, wherein X is trifluoromethyl or methoxy.

20. The method as claimed in claim 1, wherein said N-alkyl-bishydroxyethylamine is of the formula (II)

(II)

where Y is an unsubstituted or substituted $C_1$–$C_4$-alkyl.

21. The method as claimed in claim 20, wherein Y is methyl, ethyl, isopropyl, 2-hydroxyethyl, 3-hydroxypropyl, 2-aminoethyl or 3-aminopropyl.

22. The method as claimed in claim 21, wherein Y is 2-hydroxyethyl or 3-aminopropyl.

23. The method as claimed in claim 1, wherein said N-aryl-N'-alkyl-piperazine is of the formula (III)

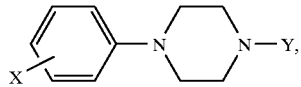

(III)

wherein X is hydrogen, halogen, $C_1$–$C_4$-alkyl, $C_1$–$C_4$-halogenoalkyl, $C_1$–$C_4$-alkoxy, $C_1$–$C_4$-halogenoalkoxy or nitro; and Y is an unsubstituted or substituted $C_1$–$C_4$-alkyl.

24. A process for preparing N-aryl-N'-alkyl-piperazines, which comprises reacting an aniline under pressure with an N-alkyl-bishydroxyethyl-amine in the presence of a strong acid which is a monohydrate of $SO_3$.

* * * * *

UNITED STATES PATENT AND TRADEMARK OFFICE
CERTIFICATE OF CORRECTION

PATENT NO. : 5,922,874
DATED : July 13, 1999
INVENTOR(S) : J. Komoschinski et al.

It is certified that error appears in the above-identified patent and that said Letters Patent is hereby corrected as shown below:

Claim 8,
Line 1, delete "5" and substitute -- 7 -- in its place.

Claim 10,
Line 1, delete "6" and substitute -- 9 -- in its place.

Claim 12,
Line 1, delete "7" and substitute -- 11 -- in its place.

Signed and Sealed this

Eighteenth Day of September, 2001

Attest:

*Nicholas P. Godici*

NICHOLAS P. GODICI
*Attesting Officer*   *Acting Director of the United States Patent and Trademark Office*